APPARATUS FOR SUCCESSIVELY FORMING DISPOSABLE DIAPERS
Original Filed March 9, 1970 10 Sheets-Sheet 1
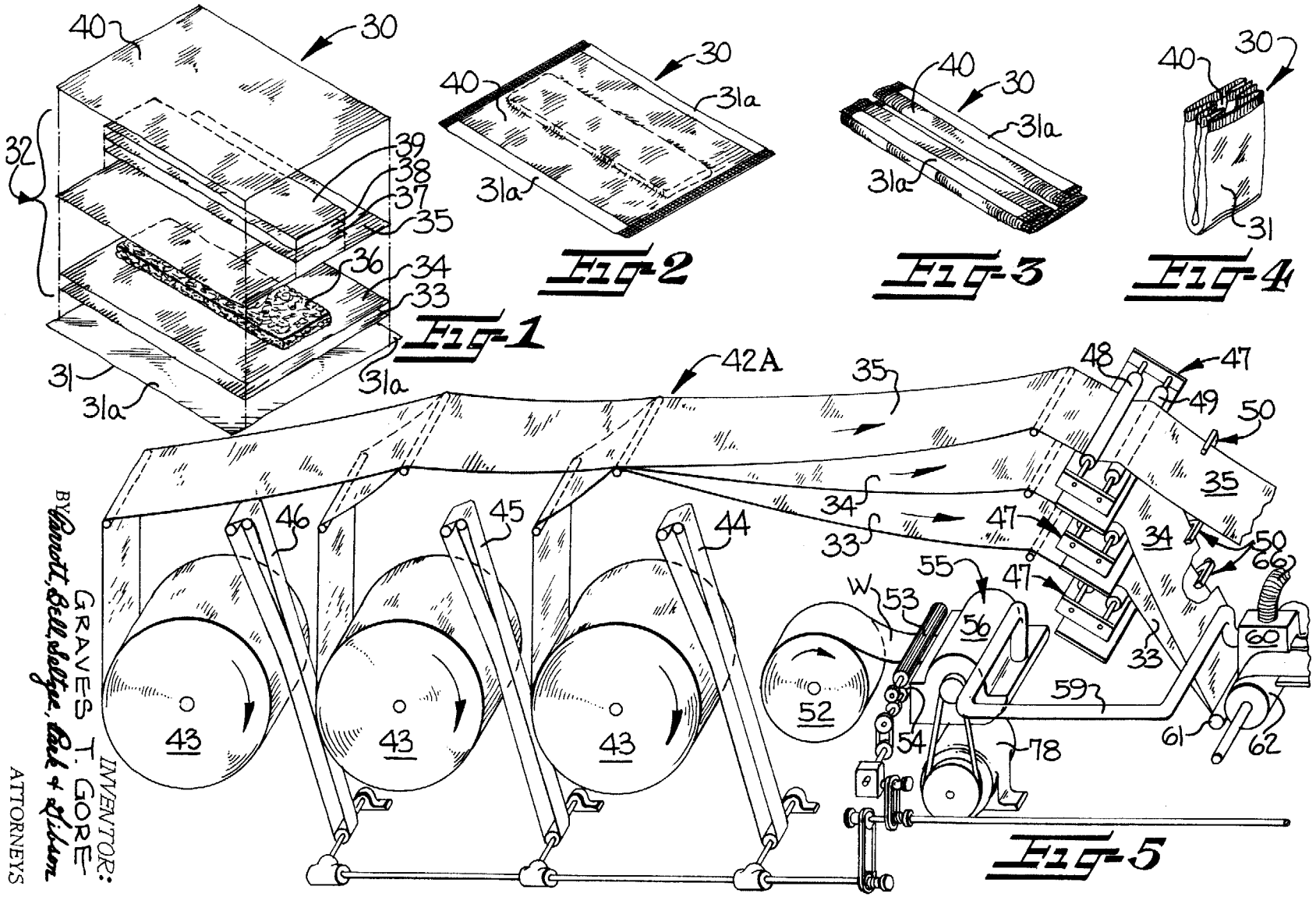
INVENTOR:
GRAVES T. GORE
BY Parrott, Bell, Seltzer, Park & Gibson
ATTORNEYS

APPARATUS FOR SUCCESSIVELY FORMING DISPOSABLE DIAPERS

Original Filed March 9, 1970 10 Sheets-Sheet 2

INVENTOR:
GRAVES T. GORE
By Pennie, Bell, Seltzer, Park & Gibson
ATTORNEYS

APPARATUS FOR SUCCESSIVELY FORMING DISPOSABLE DIAPERS

Original Filed March 9, 1970 10 Sheets-Sheet 5

INVENTOR:
GRAVES T. GORE
BY Parrott, Bell, Seltzer, Park & Gibson
ATTORNEYS

APPARATUS FOR SUCCESSIVELY FORMING DISPOSABLE DIAPERS

Original Filed March 9, 1970 10 Sheets-Sheet 4

INVENTOR:
GRAVES T. GORE

BY Parrott, Bell, Seltzer, Park & Gibson
ATTORNEYS

APPARATUS FOR SUCCESSIVELY FORMING DISPOSABLE DIAPERS

Original Filed March 9, 1970 10 Sheets-Sheet 5

INVENTOR:
GRAVES T. GORE

BY Barrett, Bell, Seltzer, Park & Gibson
ATTORNEYS

APPARATUS FOR SUCCESSIVELY FORMING DISPOSABLE DIAPERS

Original Filed March 9, 1970 10 Sheets-Sheet 6

INVENTOR:
GRAVES T. GORE

BY Parrott, Bell, Seltzer, Park & Gibson
ATTORNEYS

APPARATUS FOR SUCCESSIVELY FORMING DISPOSABLE DIAPERS

Original Filed March 9, 1970 10 Sheets-Sheet 7

INVENTOR:
GRAVES T. GORE
By Parrott, Bell, Seltzer, Park & Gibson
ATTORNEYS

APPARATUS FOR SUCCESSIVELY FORMING DISPOSABLE DIAPERS

Original Filed March 9, 1970 10 Sheets-Sheet 8

INVENTOR:
GRAVES T. GORE

BY Parrott, Bell, Seltzer, Park & Gibson
ATTORNEYS

APPARATUS FOR SUCCESSIVELY FORMING DISPOSABLE DIAPERS

Original Filed March 9, 1970 10 Sheets-Sheet 9

INVENTOR:
GRAVES T. GORE

BY Parrott, Bell, Seltzer, Park & Gibson
ATTORNEYS

APPARATUS FOR SUCCESSIVELY FORMING DISPOSABLE DIAPERS

Original Filed March 9, 1970 10 Sheets-Sheet 10

INVENTOR:
GRAVES T. GORE

BY Parrott, Bell, Seltzer, Park & Gibson
ATTORNEYS

United States Patent Office

Re. 28,139
Reissued Aug. 27, 1974

28,139
APPARATUS FOR SUCCESSIVELY FORMING DISPOSABLE DIAPERS

Graves T. Gore, Aiken, S.C., assignor to Riegel Textile Corporation, Ware Shoals, S.C.

Original No. 3,661,680, dated May 9, 1972, Ser. No. 17,594, Mar. 9, 1970. Application for reissue Nov. 30, 1972, Ser. No. 310,851
Int. Cl. B31f *7/00*
U.S. Cl. 156—467 17 Claims

Matter enclosed in heavy brackets [ ] appears in the original patent but forms no part of this reissue specification; matter printed in italics indicates the additions made by reissue.

ABSTRACT OF THE DISCLOSURE

An apparatus for successively forming disposable diapers including means for supplying an elongate moisture absorbent pad and for feeding it along a predetermined longitudinal path of travel, means for supplying and positioning an elongate fluid permeable front cover sheet in superimposed relation to one side of the pad and means for supplying and positioning an elongate backing sheet in superimposed relation to the other side of the pad. Means are provided for receiving and feeding the superimposed front cover sheet, pad and backing sheet along a predetermined longitudinal path of travel, while additional means cooperate therewith for longitudinally sealing the side portions of the superimposed components, for transversely sealing the superimposed components at predetermined longitudinally spaced intervals to form successively interconnected diapers and for severing the same along susccessive transverse seals to form individual diapers.

This invention relates to an apparatus for successively forming disposable diapers wherein each diaper includes a fluid permeable front cover sheet, a moisture absorbent pad superimposed on the front cover sheet and a backing sheet, preferably of moisture impervious material, superimposed on the other side of the pad and secured to the front cover sheet along longitudinal and transverse edges thereof.

More particularly, apparatus of this invention is specifically constructed for successively forming prefolded diapers as disclosed in U.S. patent application Ser. No. 796,478, filed Feb. 4, 1969, now abandoned entitled "Disposable Prefolded Combination Flushable Diaper and Moisture Impervious Backing" and assigned to the assignee of the present invention. Briefly stated, the prefolded combination diaper and backing disclosed in the above referred to application comprises a fluid permeable front cover sheet for being positioned against the skin of the wearer to allow moisture to pass internally of the diaper and which has high dry strength, wet hang, and dispersibility characteristics when agitated in a large excess of water and an interior pad of moisture absorbent material superimposed on the front cover sheet for absorbing moisture receiving through the front cover sheet. A moisture impervious backing sheet is superimposed on the interior pad for preventing moisture from passing therefrom and the front cover sheet, pad and backing sheet are secured in superimposed relation along longitudinal and transverse edges thereof.

Preferably, opposite side portions of the diaper are each folded inwardly over the central portion thereof along first longitudinally extending fold lines adjacent the central portion thereof and the outer sections of the thus folded side portions are each folded outwardly back over themselves along second longitudinally extending fold lines located between or intermediate the first fold lines and the longitudinal side edges of the unfolded diaper to form generally a box pleat configuration.

Thus, it is the object of this invention to provide an apparatus for forming a disposable diaper, preferably of the type briefly described above, which is capable of successively forming the same at a high capacity and at a minimum of cost to the manufacturer thereof and which apparatus avoids manual handling of individual diapers by an operator which handling is highly undesirable for reasons that are apparent.

In accordance with this invention, the apparatus may include means for supplying an elongate moisture absorbent pad and feeding it along a substantially predetermined longitudinal path of travel, means cooperating with pad supplying and feeding means for supplying and positioning an elongate fluid permeable front cover sheet in superimposed relation to one side of the pad, and means cooperating with the pad supplying and feeding means for supplynig and positioning an elongate backing sheet, preferably having a width in excess of the width of the pad and front cover sheet, in superimposed relation to the other side of the pad, preferably with opposite longitudinal side portions thereof extending transversely beyond opposite longitudinal side edges of the pad and front cover sheet. The apparatus further includes means cooperating with the pad, front cover sheet and backing sheet supplying and feeding means for receiving and feeding the superimposed front cover sheet, pad and backing sheet along a predetermined longitudinal path of travel through the remaining apparatus of this invention.

Preferably, folding means are provided which cooperate with the receiving and feeding means for folding opposite longitudinal side portions of the backing sheet around longitudinal side edges of the pad and front cover sheet in overlapping relation to marginal longitudinal side portions of the front cover sheet. Securing means secure the overlapping side portions of the backing sheet and front cover sheet to each other and means cooperate with the receiving and feeding means for transversely sealing the front cover sheet, pad and backing sheet in superimposed relation at predetermined longitudinally spaced intervals to form successively interconnected diapers. Additionally, means cooperate with the transverse sealing means for severing the same along successive transverse seals to form individual diapers.

In the preferred arrangement, the apparatus includes means for folding opposite longitudinal side portions of the superimposed front cover sheet, pad and backing sheet inwardly and over a central portion of same along first longitudinally extending fold lines and the outer sections of the side portions outwardly back over the inner sections of the side portions along second longitudinally extending fold lines and means for transversely folding the superimposed front cover sheet, pad and backing sheet intermediate adjacent transverse seals to complete the formation of the prefolded diaper having a generally box pleat configuration.

The pad supplying and feeding means may comprise means for supplying at least one and preferably a plurality of elongate moisture absorbent sheets, positioning them in superimposed relation and feeding them along a substantially predetermined longitudinal path of travel, means for supplying an elongate web of moisture absorbent fibrous material and feeding it along a substantially predetermined path of travel, a fiberizing chamber disposed in the path of the fibrous web for receiving and fiberizing it into generally individual fibers, and means including suction means communicating with the fiberizing chamber for withdrawing the fiberized fibers therefrom and depositing the fibers in superimposed batt form on a longitudinally extending central portion of the one or more moisture absorbent sheets to form the moisture absorbent pad. In addition, means may be provided for supplying an additional elongate moisture absorbent sheet and positioning it in superimposed relation to the other side of the fiber batt.

Some of the objects of the invention having been stated, other objects will appear as the description proceeds when taken in connection with the accompanying drawings, in which:

FIG. 1 is an exploded, schematic, perspective view illustrating the various components of a diaper that may be formed with the apparatus of this invention;

FIG. 2 is a perspetcive view of a diaper formed from the components of FIG. 1 prior to folding thereof;

FIG. 3 is a perspective view of the diaper of FIG. 2 wherein the diaper has been partially folded into a desired prefolded condition;

FIG. 4 is a perspective view of the diaper of FIG. 3 folded into a desired prefolded condition;

FIGS. 5–8 are schematic perspective views of successive portions of the apparatus of the present invention for forming a prefolded diaper as illustrated in FIG. 4;

Figure 6:
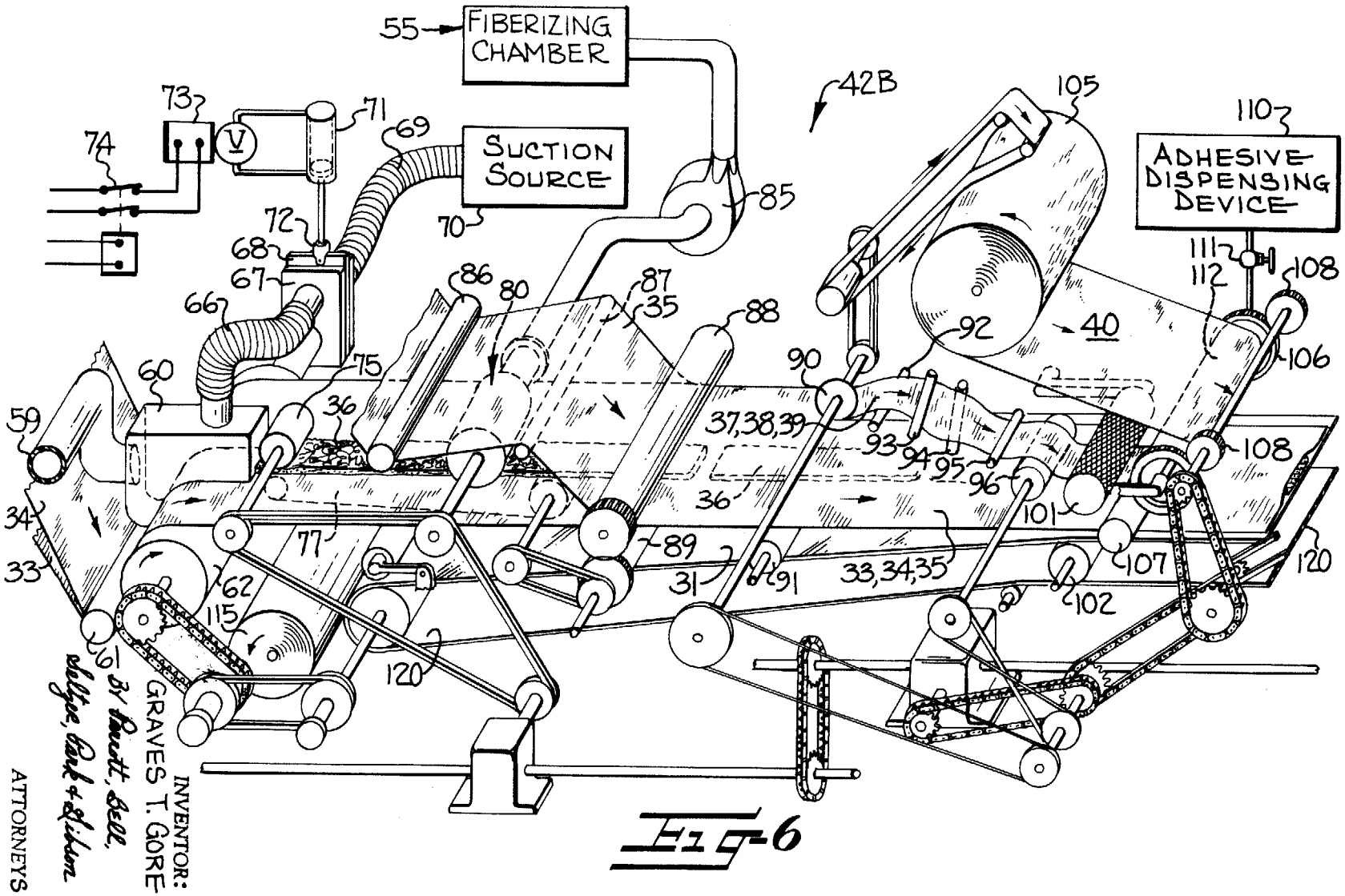

Referring specifically to FIG. 1, there is illustrated in an exploded schematic view the various components of a disposable diaper, generally designated at 30, formable with the apparatus to be hereinafter described. The lowermost component is preferably a moisture impervious backing sheet 31 formed of plastic, rubber or the like moisture impervious material and is of generally rectangular configuration. Superimposed on the backing sheet 31 is a moisture absorbent pad, generally indicated at 32, and which comprises three moisture absorbent sheets 33, 34 and 35 of uniform size disposed in superimposed relation with a fiber batt 36 disposed centrally between sheets 34 and 35 and extending longitudinally substantially the length thereof.

The pad 32 additionally includes three superimposed strips 37, 38 and 39 of moisture absorbent material superimposed on moisture absorbent sheet 35 centrally thereof in registry with the fiber batt 36. The fiber batt 36 and moisture absorbent strips 37, 38 and 39 cooperate to provide increased moisture absorbency potential centrally of the moisture absorbent pad 32. Finally, a front cover sheet 40 of fluid permeable material such as a self-bonding fibrous material or the like is superimposed on the moisture absorbent pad 32 to complete the components of the diaper 30. As illustrated in FIG. 1, backing sheet 31 preferably has a width greater than that of the moisture absorbent pad 32 and front cover sheet 40 with the pad 32 and front cover sheet 40 being superimposed centrally of the backing sheet 31 so that longitudinal side portions 31a extend outwardly beyond longitudinal edges of the other components of the diaper 30.

With reference to FIG. 2, longitudinal side portions 31a of the backing sheet 31 are folded around longitudinal side edges of the moisture absorbent pad 32 and front cover sheet 40 in overlapping relation to marginal longitudinal side portions of front cover sheet 40 with the overlapping side portions being adhesively sealed to secure the backing sheet 31 to the front cover sheet 40 along longitudinal edges of the diaper 30.

In addition, the superimposed backing sheet 31, pad 32 and front cover sheet 40 are secured in superimposed relation along transversea edges of the diaper 30.

With the superimposed backing sheet 31, pad 32 and front cover sheet 40 secured in superimposed relation along longitudinal and transverse edges as illustrated in FIG. 2, the diaper is successively folded as illustrated in FIGS. 3 and 4. That is, opposite longitudinal side portions of the diaper 30 are folded inwardly over the central portion of the same along first longitudinally extending fold lines and outer sections of the side portions are folded outwardly back over inner sections of the side portions along second longitudinally extending fold lines to provide the folded diaper 30 of FIG. 3. Thereafter, as illustrated in FIG. 4, the diaper 30 is folded transversely thereof intermediate transverse edges to complete the folding thereof and form the prefolded diaper 30 formable with the apparatus to be hereinafter described. As stated above, this diaper is of the general type disclosed in aforesaid copending application, assigned to the assignee of the present application, and reference thereto may be had for further details of the diaper construction.

While the apparatus of the present invention is specifically constructed for successively forming diapers 30 of the type just described, it will be apparent that other diapers or the like may be formed with the apparatus by making changes that will be apparent to one skilled in the art.

Successive portions of the apparatus, generally indicated at 42A–42D, are schematically illustrated in FIGS. 5–8. With reference first to FIG. 5, three continuous sheets 33, 34 and 35 of uniform width and formed of a moisture absorbent material such as highly moisture absorbent, creped tissue paper are supplied from three supply rolls 43, which supply rolls are frictionally engaged and rotatably driven, as illustrated, by respective continuous conveyor belts 44, 45, and 46. Conveyor belts 44, 45 and 46 are driven in synchronism with each other by a common drive to supply and feed sheets 33, 34 and 35 at the same rate.

The continuous moisture absorbent sheets 33, 34 and 35 are fed along substantially predetermined longitudinal paths of travel along which each of the continuous sheets 33, 34 and 35 passes through respective identical aliging means, generally indicated at 47, which align the sheets 33, 34 and 35 directly above each other for thereafter feeding into superimposed relation. The aligning means 47 are of conventional construction and, accordingly, will not be described in detail. It suffices to say that each of the sheets 33, 34 and 35 passes between a pair of cooperating rolls 48 and 49 which rolls are laterally shiftable in response to the sensing of the position of the respective sheet by a sensing head 50 which causes the rolls 48 and 49 to be shifted to maintain the respective sheet in alignment with the others and advancing along a predetermined path of travel.

Figure 9:
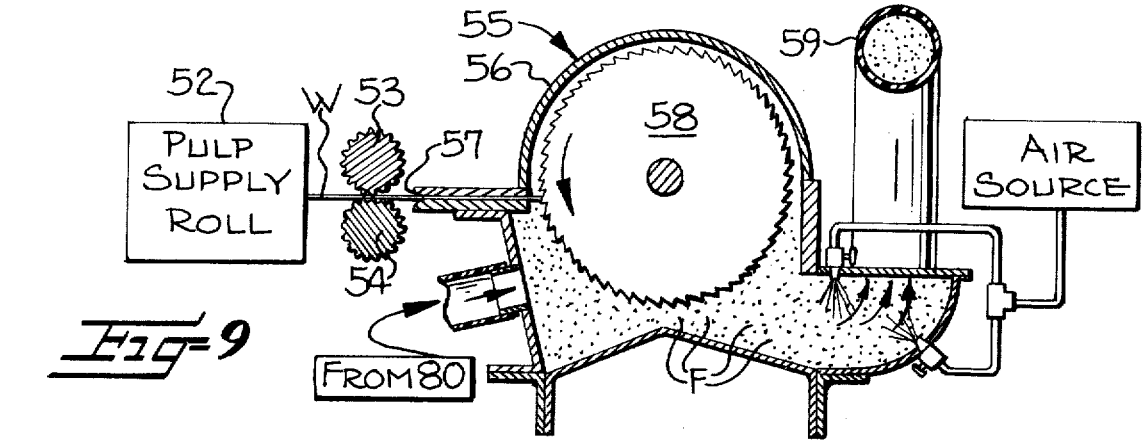
FIG. 9 is an enlarged schematic, elevational view with parts in section of a portion of the apparatus of FIG. 5 and illustrating the fiberizing chamber for the fibrous web.

Simultaneously with the feeding of the moisture absorbent sheets 33, 34 and 35, a continuous web W of moisture absorbent fibrous material such as wood pulp is supplied from a supply roll 52 and fed along a predetermined longitudinal path of travel by a pair of cooperating nip feed rolls 53 and 54 into a fiberizing chamber 55, suitably disposed in the path of the fibrous web W. With reference to FIG. 9, the fiberizing chamber 55 comprises a housing 56 having an inlet 57 disposed adjacent nip feed rolls 53 and 54 for receiving the fibrous web W therefrom into housing 56. Inwardly of housing 56, a fiberizing roll 58 is mounted for driving rotation by means such as motor 78, FIG. 5, so as to disintegrate or fiberize the fibrous web W into individual fibers as it is fed into the fiberizing chamber 55 to form fiberized fibers F. A conduit 59 communicates with the fiberizing chamber 55 and extends therefrom to a housing 60, FIG. 5, to be hereinafter more fully described.

Figure 10:
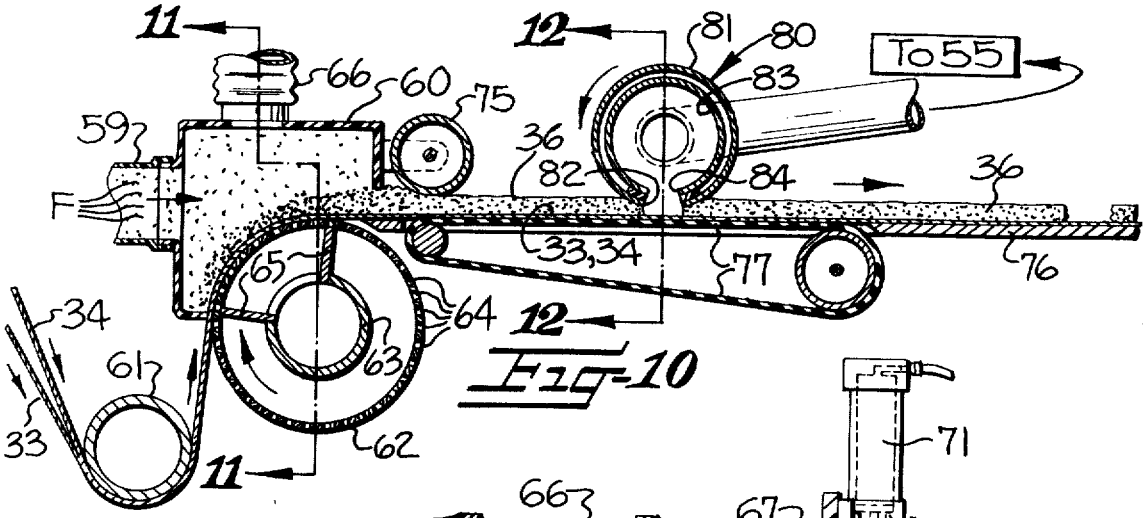
FIG. 10 is an enlarged, schematic, elevational view with parts in section of a portion of the apparatus of FIG. 6 and illustrating the means including suction means that communicate with the fiberizing chamber for depositing the fiber batt in superimposed relation on a longitudinally extending portion of the at least one moisture absorbent sheet.
Figure 11:
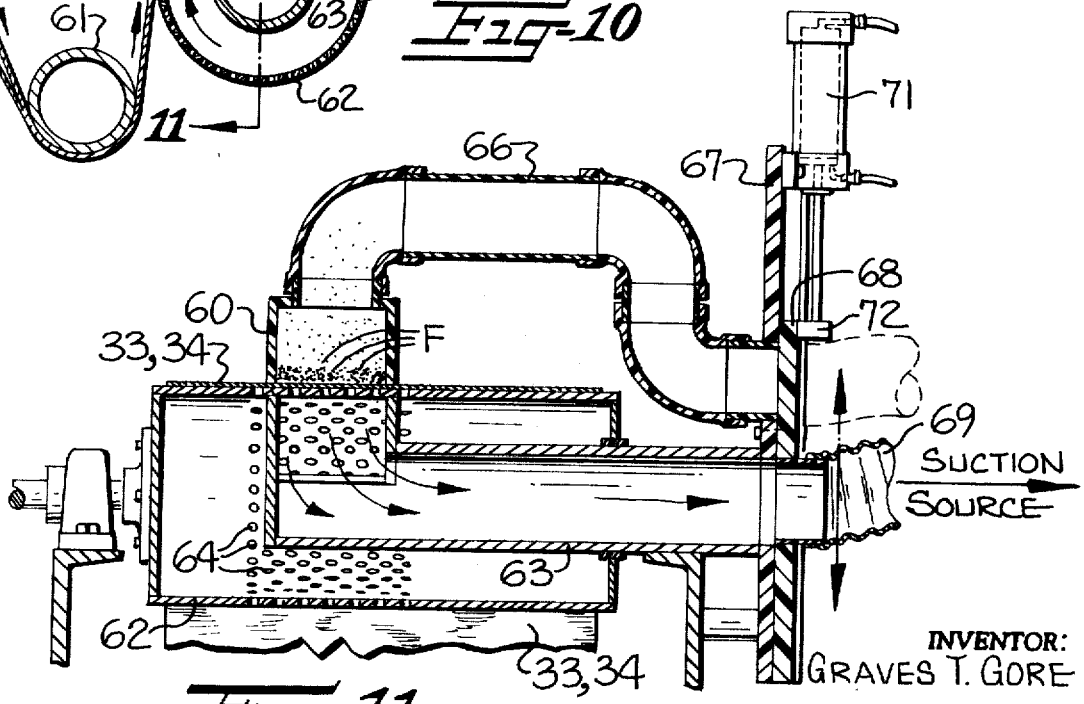
FIG. 11 is a sectional view taken substantially along the line 11—11 of FIG. 10.

As illustrated in the right-hand portion of FIG. 5 and likewise, in the left-hand portion of FIG. 6, absorbent sheets 33 and 34 are fed into superimposed relation around guide bar 61 onto a hollow cylindrical rotatably driven roll 62. Housing 60 is disposed adjacent roll 62 and conforms partially therearound with the super imposed moisture absorbent sheets 33 and 34 being received therebetween. The cooperation between housing 60 and cylindrical roll 62 is best illustrated in FIGS. 10 and 11. As there illustrated, one end of cylindrical roll 62 is rotatably mounted centrically upon conduit 63 which may be supported in any suitable manner, as shown, with the other end of roll 62 being drivingly connected for rotation thereof by drive means schematically illustrated in FIG. 6. A central portion of the hollow cylindrical roll 62 includes a plurality of circumferentially and axially spaced openings or apertures, 64, a segment of which is in open communication with conduit 63 via partition means 65.

The portion of housing 60 adjacent roll 62 is open so that housing 60 communicates through the apertures 64 in roll 62 with conduit 63. The housing 60 also has a conduit 66 communicating therewith which extends outwardly therefrom and communicates through a conduit support plate 67. Similarly, conduit 63 extends from cylindrical roll 62 and communicates through support plate 67 in spaced relation from conduit 66. A gate plate 68 having a conduit 69 communicating therethrough is mounted adjacent support plate 67 for sliding movement relative thereto for selectivity communicating conduit 69 with conduits 63 and 66. As illustrated in FIG. 6 the end of conduit 69 remote from gate plate 68 extends to and communicates with a suction source 70. Thus, gate plate 68 may be selectively positioned for applying suction directly to housing 60 and cylindrical roll 62.

A double-acting, reciprocating piston and cylinder assembly 71 is operatively connected to gate plate 68 as at 72 for selectively positioning gate plate 68 and is controlled by a solenoid actuating control valve 73 and relay switch means 74, the coil of which is preferably connected in parallel with the power source of the apparatus so that during normal operation, relay switch means 74 is closed and gate plate 68 is positioned, as shown in FIGS. 6 and 11, with suction source 70 communicating through conduits 69 and 63, the hollow cylindrical roll 62, the moisture absorbent sheets 33 and 34, and housing 60 with the fiberizing chamber 55 for withdrawing the fiberized fibers F therefrom. Thus, during normal operation, fiberized fibers F are drawn from fiberizing chamber 55 and deposited longitudinally along the superimposed moisture absorbent sheets 33 and 34 to form a longitudinally extending fiberized batt 36, as illustrated in FIG. 6. Removal of the fiberized fibers F from the fiberizing chamber 55 is facilitated by establishing suitable air jets as schematically illustrated in FIG. 9 in the fiberzing chamber 55. Once the power to the apparatus is cut off and the feeding of the moisture absorbent sheets 33 and 34 stops, the relay switch means 74 will open to position gate plate 68 as shown in phantom lines in FIG. 11 so that suction source 70 is in direct communication with housing 60 to draw the excess fiberized fibers F from fiberizing chamber 55 into the suction source 70. Thus, cutting off the power to the apparatus, the fiberized fibers F in the fiberizing chamber 55 will not be drawn therefrom to accumulate in the housing 60 against the moisture absorbent sheets 33 and 34, which accumulation would present problems to renewed operation of the apparatus.

Figure 12:
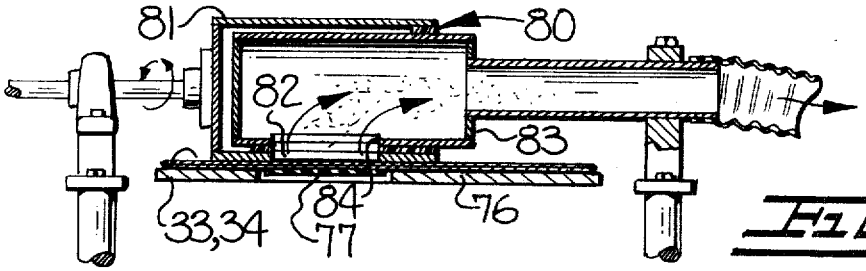
FIG. 12 is a sectional view taken substantially along the line 12—12 of FIG. 10.

As the superimposed moisture absorbent sheets 33 and 34 and the fiberized batt 36 emerge from between housing 60 and cylindrical roll 62, they pass between a compressing roll 75 and support plate 76, FIG. 10, where they are compressed to condense the fiberized batt 36. To facilitate in feeding of superimposed sheets 33 and 34 and fiberized batt 36, a conveyor 77 communicates through an opening in support plate 76 and positively feeds the same along a predetermined path of travel. While still being supported by support plate 76 and fed by conveyor 77, the superimposed moisture absorbent sheets 33 and 34 and the fiberized batt 36 pass beneath means, generally indicated at 80 and best illustrated in FIGS. 10 and 12, for removing transverse segments of the fiberized batt 36. The removing means 80 comprises a rotatably driven hollow cylindrical member 81 having a slot 82 extending longitudinally thereof and a conduit 83 mounted therewithin and being connected to cylindrical member 81 for rotation of cylindrical member 81 relative thereto. Conduit 83 includes an elongate slot 84 disposed therein adjacent the fiberized batt 36 which slot 84 communicates with slot 82 once during each revolution of cylindrical member 81. Conduit 83 communicates, as illustrated, through a suction source 85 with fiberizing chamber 55. Thus, during each revolution of cylindrical member 81, the suction of suction source 85 will be applied to the fiberized batt 36 superimposed on superimposed moisture absorbent sheets 33 and 34 and remove a transverse segment thereof and convey the same back to the fiberizing chamber 55 for reprocessing. Preferably, the cylindrical member 81 is rotatably driven such that the periphery of the cylindrical member 81 is moving at the same rate as the superimposed moisture absorbent sheets 33 and 34 and fiberized batt 36 is being fed with the circumstance of the cylindrical member 81 being substantially equal to the length of one diaper 30 being formed. Thus, it will be apparent that at longitudinally spaced intervals corresponding to the length of the diaper 30 being formed, transverse segments of the fiberized batt 36 will be removed for reasons that will become apparent upon further description of the present invention.

During the depositing of the fiberized batt 36 on the superimposed moisture absorbent sheets 33 and 34 and removal of transverse segments thereof from the moisture absorbent sheets 33 and 34, moisture absorbent sheet 35 is being continuously fed thereabove under guide bar 86 and over guide bar 87, FIG. 6. Moisture absorbent sheet 35 is now positioned in superimposed relation with the other side of the fiberized batt 36 and passed with the fiberized batt 36 and moisture absorbent sheets 33 and 34 between nip feed rolls 88 and 89 which feed rolls 88 and 89 facilitates in the feeding of the moisture absorbent sheets 33, 34 and 35 along their respective predetermined longitudinal paths of travel. Downstream from nip feed rolls 88 and 89, a rotary cutter 90 cooperating with an anvil 91 trims superimposed longitudinal side portions 37, 38 and 39, respectively, from the three moisture absorbent sheets 33, 34 and 35 which trimmed side portions 37, 38 and 39 are thereafter positioned by cooperating guide rods 92, 93, 94, 95 and guide roll 96 in superimposed relation to the moisture absorbent sheets 33, 34 and 35 and fiberized batt 36 to complete the formation of the moisture absorbent pad 32, as heretofore described and schematically illustrated in FIG. 1.

Figure 13:
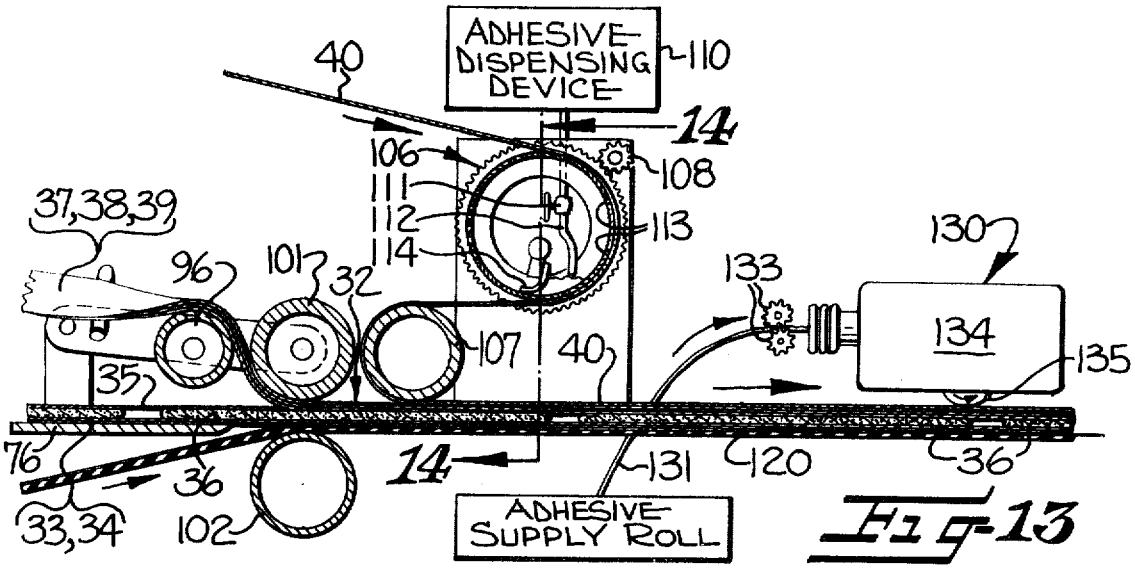
FIG. 13 is an enlarged, schematic, elevational view with parts in section of a portion of the apparatus of FIG. 6 illustrating the means for applying adhesive to one side of the front cover sheet to facilitate its securement to the moisture absorbent pad and means for applying adhesive to one of the marginal longitudinal side portions of the front cover sheet.
Figure 14:
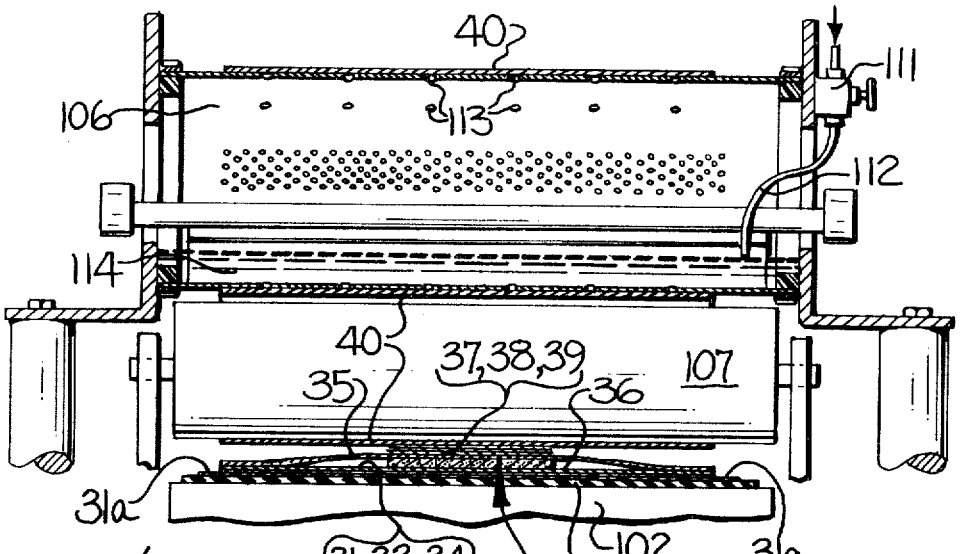
FIG. 14 is a sectional view taken substantially along the line 14—14 of FIG. 13.

The moisture absorbent pad 32 passes, as best shown in FIGS. 6 and 13, beneath a pressure roll 101 which cooperates with pressure roll 102 to compress the moisture absorbent pad 32 into a compact form. Immediately above the advancing moisture absorbent pad 32 is a supply roll 105 of a continuous fluid permeable front cover sheet 40. The continuous fluid permeable front cover sheet 40 is fed by suitable conveyor means, as illustrated, from supply roll 105 and drawn around an adhesive applying roll 106 and guide bar 107 and positioned in superimposed relation to the moisture absorbent pad 32. The adhesive applying roll 106, as best illustrated in FIGS. 13 and 14, is suitably supported for rotation about its longitudinal axis and includes adjacent each end thereof gear connections 108 which provide means for driving rotation of adhesive applying roll 106 at the same rate as the moisture absorbent pad 32. A liquid adhesive is supplied from an adhesive dispensing device 110 through valve 111 internally of adhesive applying roll 106 via conduit 112. The body of the adhesive applying roll 106 includes a plurality of axially and circumferentially spaced openings or apertures 113 through which the adhesive may emerge. Gravity causes the adhesive to settle in the lower portion of the adhesive applying roll 106 where a doctor blade 114 cooperates with the internal surface of the adhesive applying roll 106 to force the adhesive through the apertures 113 onto one side of the continuous fluid permeable sheet 40 as it passes therearound which side is disposed against pad 32 to adhesively secure the front sheet 40 in superimposed relation to the moisture absorbent pad 32.

A supply roll 115 preferably containing a moisture impervious backing sheet 31 having a width in excess of the width of pad 32 and front cover sheet 40 is disposed adjacent a continuous conveyor 120 which draws the continuous backing sheet 31 from supply roll 115 and feeds it along a predetermined longitudinal path of travel. The superimposed moisture absorbent pad 32 and front cover sheet 40 are received on conveyor 120 in superimposed relation to a central portion of the backing sheet 31 so that longitudinal side portions 31a of the backing sheet 31 extend outwardly beyond longitudinal edges of pad 32 and front cover sheet 40. In addition to positioning the backing sheet 31 in superimposed relation with the pad 32 and front cover sheet 40, conveyor 120 feeds the superimposed front cover sheet 40, moisture absorbent pad 32 and backing sheet 31 along a predetermined longitudinal path of travel as illustrated in FIGS. 6 and 7.

Means, generally indicated at 130, are disposed adjacent opposite longitudinal side edges of the traveling superimposed front cover sheet 40, pad 32 and backing sheet 31 for applying adhesive to opposite marginal longitudinal side portions in the front cover sheet 40. As illustrated in FIGS. 7 and 13, a strand 131 preferably of thermoplastic adhesive is drawn from an adhesive supply means such as supply roll 132 by a pair of cooperating nip feed rolls 133 into a housing 134 where the thermoplastic adhesive is heated and applied to an applicator roll 135 which applicator roll 135, as illustrated in FIG. 7, applies the adhesive along opposite marginal longitudinal side portions of the front cover sheet 40.

Figure 7:
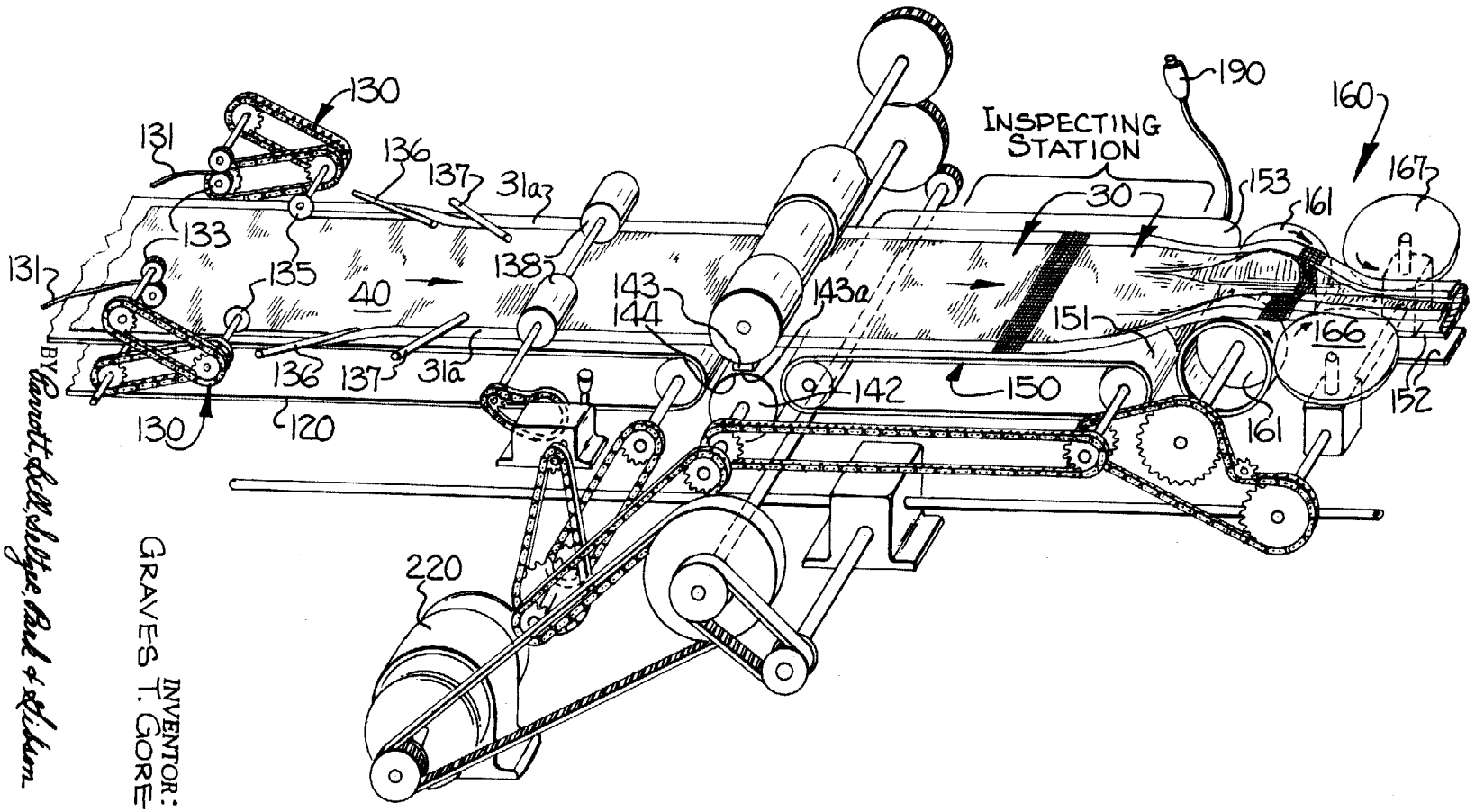

Adjacent each of the adhesive applying means 130 are a pair of cooperating folding arms 136 and 137 which folding arms 136 and 137 cooperate, as illustrated in FIG. 7, to fold longitudinal side portions 31a of the backing sheet 31 around longitudinal side edges of the pad 32 and front cover sheet 40 in overlapping relation to the marginal side portions of the front cover sheet 40 with the adhesive applied by adhesive applying means 130 being disposed therebetween for securing the overlapping portions of the front cover sheet 40 and backing sheet 31 together. To insure that the overlapping portions of the front cover sheet 40 and backing sheet 31 are secured by the adhesive, opposite longitudinal side portions of the superimposed front cover sheet 40, pad 32, and backing sheet 31 pass beneath respective pressure rolls 138 for compressing the overlapping portions together.

Adjacent conveyor 120 and after the superimposed front cover sheet 40, pad 32 and backing sheet 31 have been sealed along longitudinal edges thereof, the superimposed front cover sheet 40, pad 32 and backing sheet 31 pass from conveyor 120 between a pair of cooperating embossing rolls 141 and 142 for transversely sealing the superimposed front cover sheet 40, pad 32 and backing sheet 31 at predetermined longitudinally spaced intervals to form successively interconnected diapers 30.

Preferably, as illustrated in FIG. 7, embossing rolls 141 and 142 include cooperating embossing heads 143 and 144, respectively, and are driven in synchronism with each other as illustrated and at a rate relative to the rate of travel of the superimposed front cover sheet 40, pad 32 and backing sheet 31 to transversely emboss the same at the desired longitudinally spaced intervals in registry with the positions where transverse segments of the fiberized batt 36 were removed to facilitate the transverse sealing thereof by embossing rolls 141 and 142. In addition, embossing head 143 includes a perforating blade 143a which cuts against embossing head 144 for perforating the superimposed front cover sheet 40, pad 32, and backing sheet 31 transversely along successive transverse seals.

Figures 19, 20:
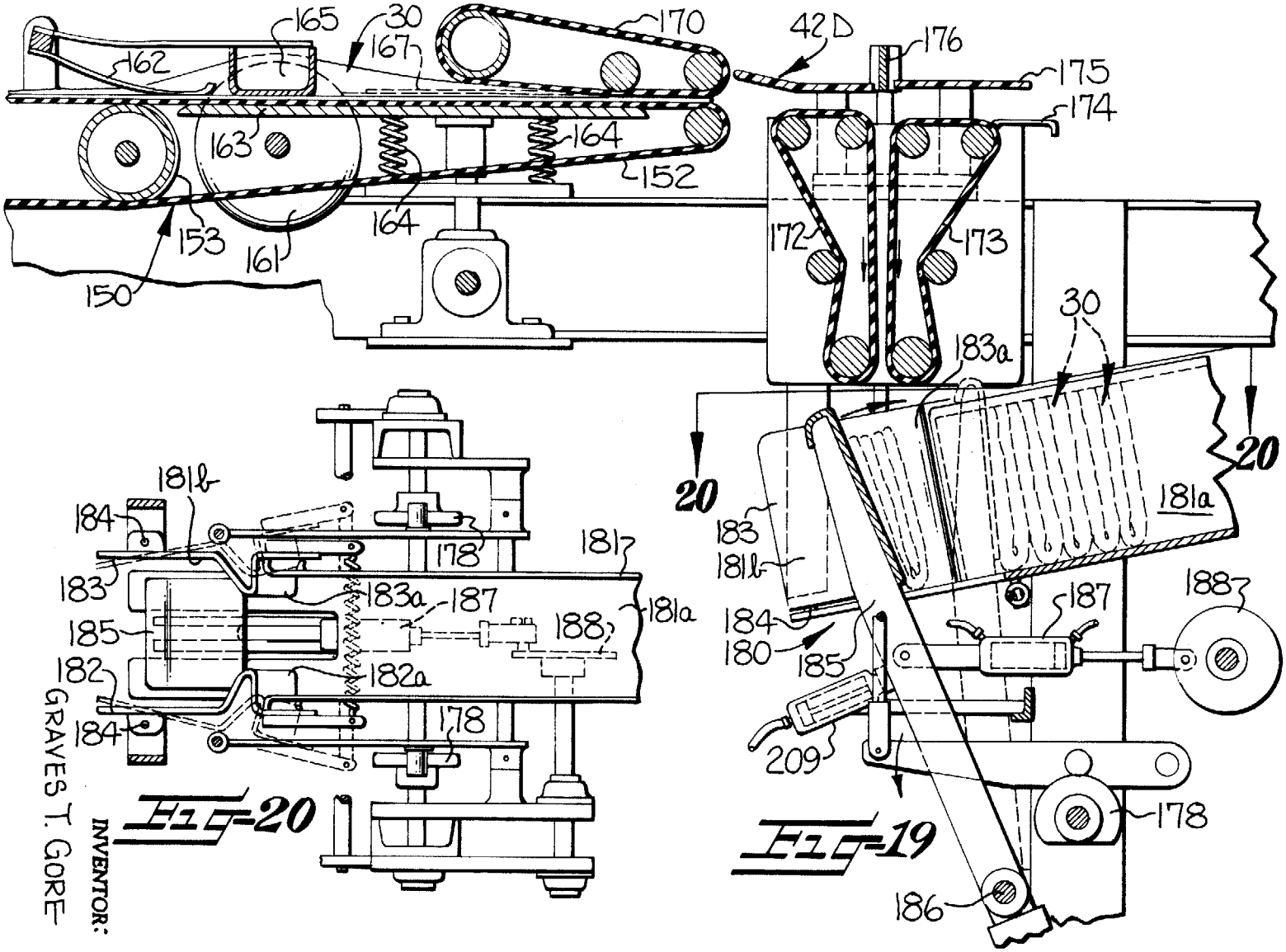
FIG. 19 is a sectional view taken substantially along the line 19–19 of FIG. 15.
FIG. 20 is a sectional view taken substantially along the line 20–20 of FIG. 19.

A continuously driven endless conveyor 150 is disposed adjacent embossing rolls 141 and 142 and cooperates therewith for receiving the successively interconnected diapers 30 therefrom for feeding them along a predetermined longitudinal path of travel. The conveyor 150, as best illustrated in FIGS. 7 and 19, includes three side-by-side portions 151, 152 and 153 with the central portion 152 thereof advancing the successively interconnected diapers 30 through means generally indicated at 160, which means operate to fold opposite longitudinal side portions of the superimposed front cover sheet 40, pad 32 and backing sheet 31 inwardly over the central portion of the same along first longitudinal extending fold lines and outer sections of the side portions outwardly back over inner sections of the side portions along second longitudinally extending fold lines to form a generally box pleat configuration, as illustrated in FIG. 3 .

Figure 16:
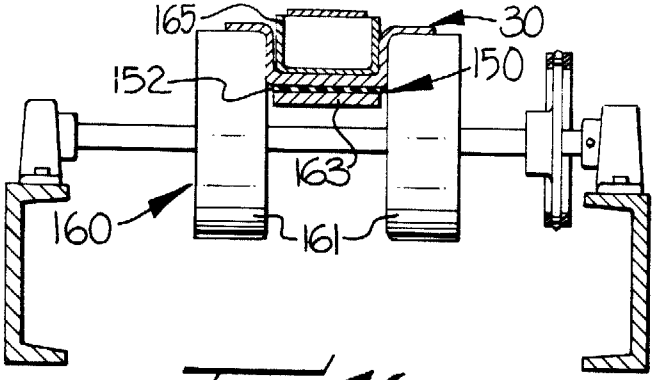
FIG. 16 is a sectional view taken substantially along the line 16—16 of FIG. 15.

More particularly, the folding means 160 comprises a pair of spaced apart cylindrical drums 161 which drums engage opposite longitudinal *side portions of the superimposed front cover sheet 40, pad 32 and backing sheet 31 to fold the longitudinal side portions along first longitudinally extending fold lines to extend substantially perpendicular to the central portion of same, as best illustrated in FIGS. 7 and 16. With reference to FIG. 19, it will be noted that as drums 161 fold the longitudinal side portions, a guide arm 162 presses the central portion of the superimposed front cover sheet 40, pad 32 and backing sheet 31 against the top run of the central portion 152 of conveyor 150 while the side portions are being folded to extend substantially perpendicular to the central portion of same. In addition, a pressure plate 163 is disposed beneath the top run of the central portion 152 of conveyor 150 in supporting relation thereto for supporting the superimposed front cover sheet 40, pad 32 and backing sheet 31 passing thereover to facilitate the folding thereof. As illustrated in FIG. 19, the pressure plate 163 is spring biased by coil springs 164 upwardly against the top run of conveyor 150. A box-like conforming member 165, FIGS. 16 and 19, is disposed between the spaced apart hollow drums 161 and cooperates therewith to in-*

*sure that opposite longitudinal side portions of the superimposed front cover sheet 40, pad 32 and backing sheet 31 are folded along first longitudinal extending fold lines to extend substantially perpendicular to the central portion of same.*

Figure 8:
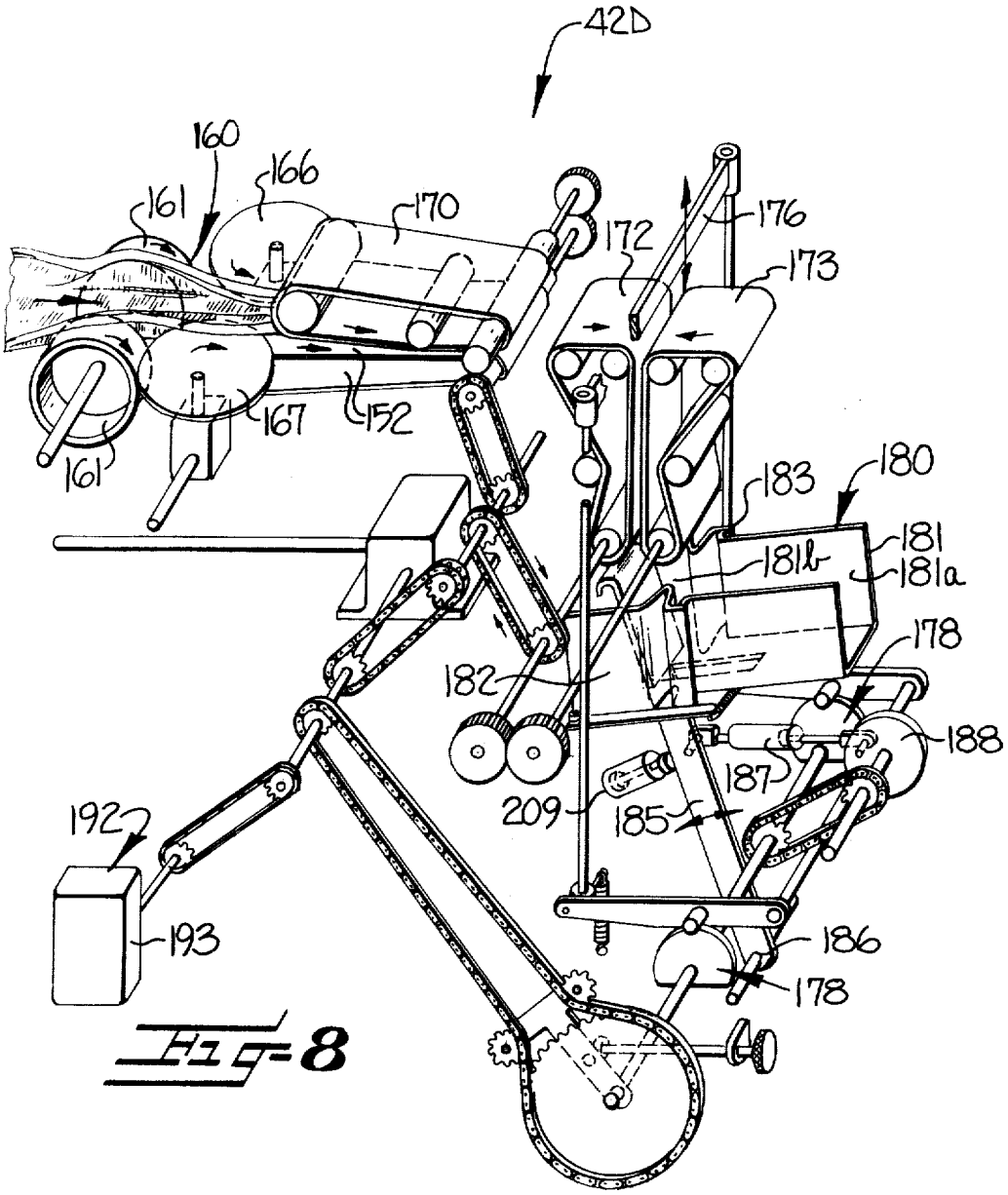
Figure 15:
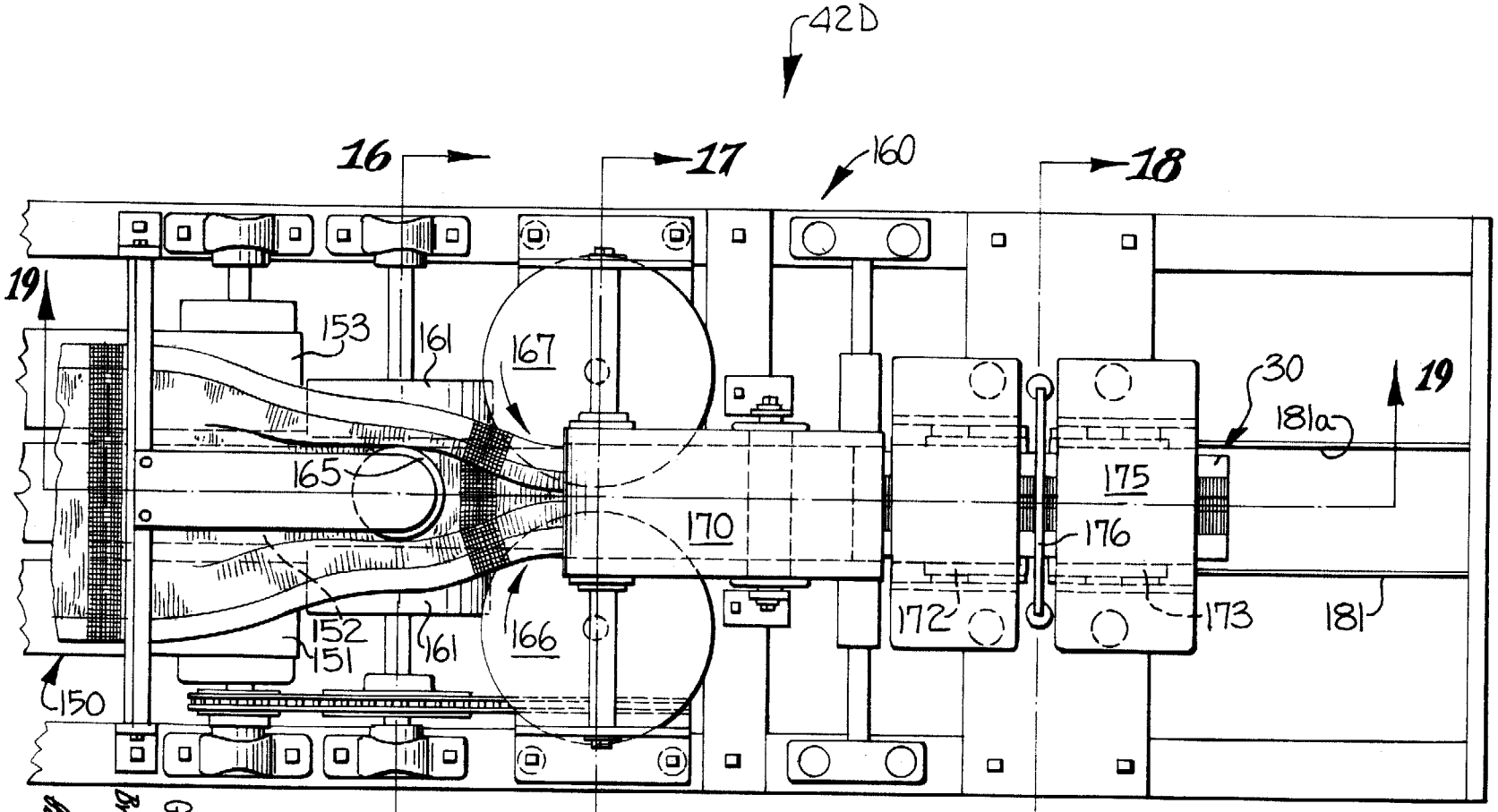
FIG. 15 is an enlarged, schematic, top plan view of the portion of the apparatus of FIG. 8.
Figure 18:
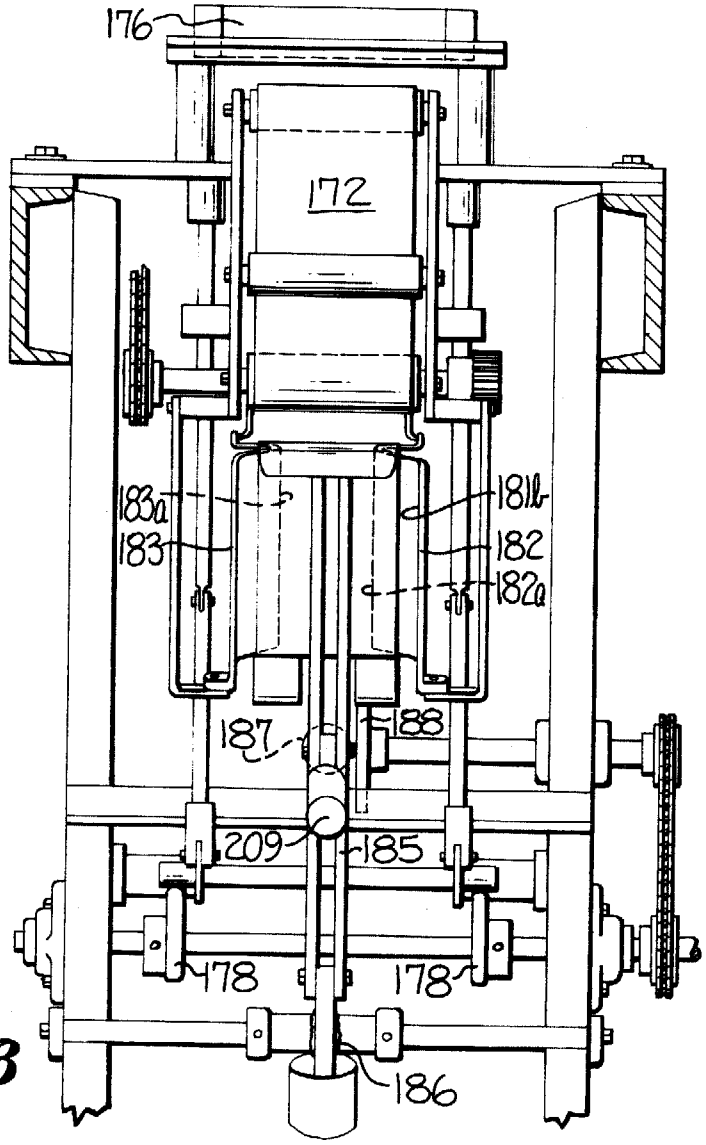
FIG. 18 is a sectional view taken substantially along the line of 18–18 of FIG. 15.
Figure 17:
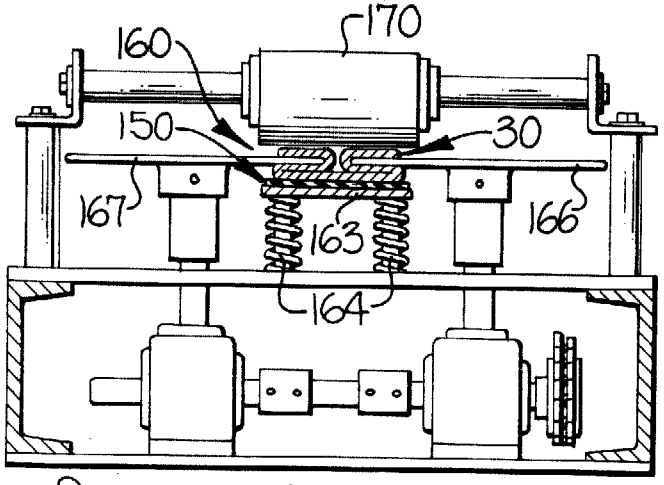
FIG. 17 is a sectional view taken substantially along the line of 17–17 of FIG. 15.

Immediately thereafter, a pair of spaced apart rotatably driven discs or cams 166 and 167 are disposed for rotation in a plane perpendicular to the thus folded opposite longitudinal side portions of the superimposed front cover 40, pad 32 and backing 31 and engage the same to inwardly fold, FIGS. 8, 15 and 17, the opposite longitudinal side portions along second longitudinally extending fold lines positioned intermediate the first fold lines and side edges of same with the outer sections of the side portions overlapping inner sections of the side portions. A continuous conveyor 170 is superimposed on a portion of conveyor 150 above discs 166 and 167 and cooperates therewith during the inward folding for receiving the folded, successively interconnected diapers 30 therebetween and for positive feeding thereof along a predetermined longitudinal path of travel.

From conveyors 150 and 170, the folded, successively interconnected diapers 30 are separated into individual diapers 30 along successive transverse seals and perforations and are transversely folded intermediate adjacent transverse edges to complete the formation of the prefolded diapers 30.

More particularly, with reference to FIGS. 8 and 19, a pair of cooperating, side-by-side, endless conveyors 172 and 173 are disposed adjacent superimposed conveyors 150 and 170 and extend substantially perpendicular thereto. A pair of spaced apart guide plates 174 and 175, FIG. 19, are disposed immediately adjacent superimposed conveyors 150 and 170 parallel thereto for receiving the successively interconnected diapers 30 therebetween. Each of the guide plates 174 and 175 includes an opening or passage therethrough which communicates with each other and the space between side-by-side conveyors 172 and 173 for reasons soon to become apparent. A transfer arm 176 is disposed for communication with the openings in guide plates 174 and 175 and is adapted for reciprocating movement therebetween and between side-by-side conveyors 172 and 173 for transferring the successively interconnected diapers 30 received between guide plates 174 and 175 between side-by-side conveyors 172 and 173.

More particularly, transfer arm 176 is reciprocated by cam means 178, schematically illustrated in FIGS. 8 and 19, in timed relationship with the feeding of the successively interconnected diapers 30 between guide plates 174 and 175 for successively engaging the interconnected diapers 30 intermediate adjacent transverse seals and transferring this intermediate portion between side-by-side conveyors 172 and 173. Conveyors 172 and 173 are driven at a substantially faster rate than conveyors 150 and 170 and, accordingly, upon receiving the diapers 30 therebetween, cause the same to be severed along transverse perforations. In addition, the conveyors 172 and 173 complete the transverse folding of same into successive prefolded individual diapers 30, as illustrated in FIG. 4.

Immediately beneath the conveyors 172 and 173 is means for accumulating the individual prefolded diapers 30 and positioning the same in side-by-side relation for packaging or the like, the means being generaly indicated at 180.

The accumulating means 180 comprises an elongate accumulating box 181 having an accumulating portion 181a and a receiving portion 181b adjacent accumulating portion 181a and in receiving relation to conveyors 172 and 173. The receiving portion 181b includes spaced apart gate members 182 and 183, which gate members 182 and 183 have inwardly extending portions 182a and 183a, respectively, the normal distance between which is less than the width of a diaper 30 being formed with the apparatus. As illustrated in FIG. 20, the gate members 182 and 183 are pivotally connected at the ends thereof remote from the accumulating portion 181a of accumulating box 181 as at 184 and are spring biased together at the other end so that the gate members 182 and 183 may be pivoted at 184 to move the inwardly extending portions 182a and 183a outwardly for the passage of a diaper 30 from the receiving portion 181b to the accumulating portion 181a of accumulating box 181.

A stacking arm 185 is disposed through a slot in the bottom of accumulating box 181 and is mounted for pivoting movement as at 186 for movement longitudinally of accumulating box 181 from the receiving portion 181b between gate members 182 and 183 into the accumulating portion 181a and back. The stacking arm 185 is normally positioned, as shown in FIGS. 8 and 19, in the receiving portion 181b of accumulating box 181 in cooperating relation with conveyors 172 and 173 for receiving individual prefolded diapers 30 between same and the accumulating portion 181a of accumulating box 181, as illustrated in FIG. 19. The stacking arm 185 is connected intermediate its length to a piston and cylinder assembly 187 which is normally maintained in the extended position with the other end thereof being eccentrically connected to a rotating disc 188 which is rotated in timed relationship to the receiving of individual diapers 30 in the receiving portion 181b of accumulating box 181 for moving stacking arm 185 from the receiving portion 181b between gate members 182 and 183 into the accumulating portion 181a of accumulating box 181 to successively transfer the individual diapers 30 into accumulating portion 181a of accumulating box 181 where they are positioned in side-by-side relation. It will be apparent that inwardly extending portions 182a and 183a of gate members 182 and 183 normally maintain the diapers 30 in side-by-side relation in the accumulating portion 181a of accumulating box 181.

The apparatus of the present invention further includes means for ejecting an inferior or otherwise unsatisfactory diaper 30 formed thereby. With reference to FIG. 8, an inspection station may be established adjacent the path of travel of the successively interconnected diapers 30 prior to folding thereof by folding means 160. At this point, an operator may visually observe the quality of the interconnected diapers 30 and should an unsatisfactory diaper 30 be observed, a manual switch 190 may be actuated to indicate that an unsatisfactory diaper has been observed.

Figure 23:
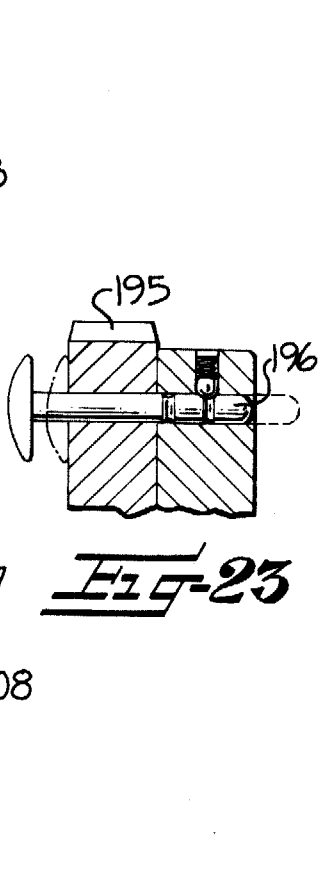
FIG. 23 is an enlarged sectional view taken substantially along the line 23–23 of FIG. 21.

Means, generally indicated at 192 in FIG. 8, is provided which is responsive to actuation of switch 190 for causing the unsatisfactory diaper 30 to be ejected. With reference to FIGS. 8 and 21–23, the means 192 comprises a housing 193 having a gear 194 mounted therein and driven in timed relationship with the receipt of individual prefolded diapers 30 in the receiving portion 181b of accumulating box 181, as illustrated in FIG. 8. A gear 195 having a diameter substantially greater than that of gear 194 meshes with and is rotated by gear 194 and includes a plurality of circumferentially and equally spaced pins 196 which are slidably mounted for movement therethrough between first and second keyed positions, as shown in FIG. 23.

Figure 22:
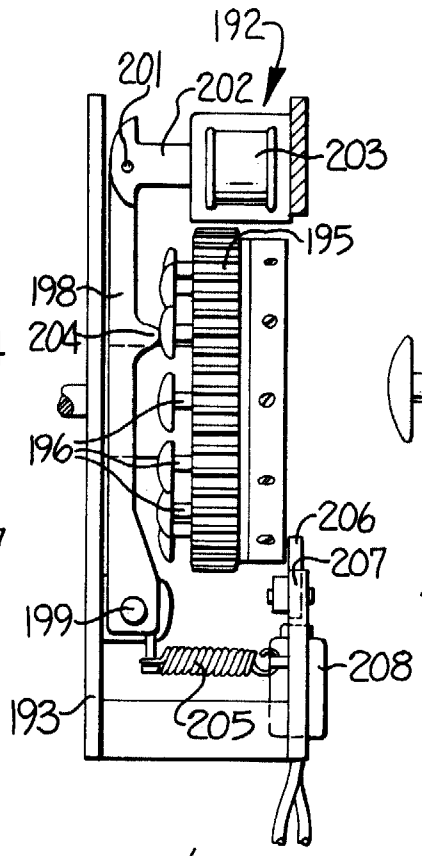
FIG. 22 is a schematic side elevational view of the portion of the apparatus illustrated in FIG. 21.
Figure 21:
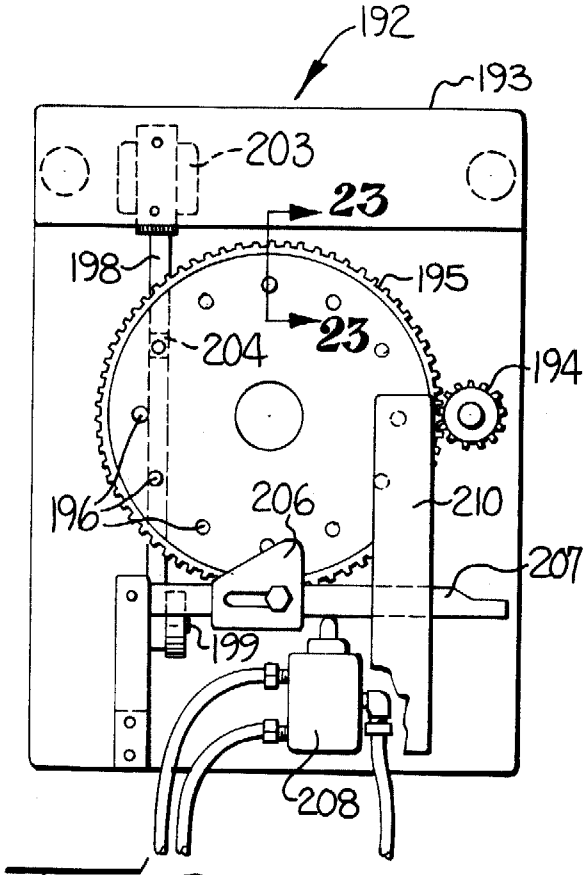
FIG. 21 is an enlarged, schematic elevational view of a portion of the apparatus of FIG. 8 and illustrating means for rejecting an unsatisfactory diaper formed by the apparatus of the present invention.

The pins 196 are spaced so that rotation of gear 195 an amount corresponding to the degrees between adjacent pins 196 is equal to the time interval in receipt of successive prefolded diapers 30 from between cooperating conveyors 172 and 173 into the receiving portion 181b of accumulating box 181. The pins 196 are normally keyed in a first position, as indicated in FIG. 23. An actuating arm 198 is pivotally mounted at one end as at 199 adjacent gear 195 and extends adjacent thereto across a segment of gear 195 whereon the other end, FIG. 22, is pivotally connected as at 201 to the free end of the core 202 of a solenoid 203. Solenoid 203 is operatively connected to switch 190 and is energized by the closing of switch 190 as by an operator upon visually observing an unsatisfactory diaper 30.

Energization of solenoid 203 causes actuating arm 198 to pivot and override the bias of spring 205 whereupon a boss 204 on actuating arm 198 depresses a pin 196 and slides it through gear 195 from the first position to a second position, as indicated in phantom lines in FIG. 23, whereon one end of the pin 196 emerges from the other side of gear 195 and is keyed in that position.

As the unsatisfactory diaper 30 advances through the remaining apparatus, gear 195 rotates to bring the depressed pin 196 having the one end projecting from gear 195 into engagement with an abutment member 206 which pivots a lever 207 to actuate an air valve 208. Air is exhausted from piston and cylinder assembly 187 and supplied to another piston and cylinder assembly 209, FIGS. 8 and 19, which causes stacking arm 185 to move from the receiving portion 181b of accumulating box 181 between gate members 182 and 183 into the accumulating portion 181a out of the normal timed operation thereof, as previously described, so that the unsatisfactory diaper 30 is received in the receiving portion 181b of accumulating box 181 behind stacking arm 185. The unsatisfactory diaper 30 is rejected through the rear end of accumulating box 181 by stacking arm 185 when pin 196 passes abutment member 206 and allows lever 207 to return to its normal position whereupon air valve 208 is actuated to supply air to piston and cylinder assembly 187 and exhaust same from piston and cylinder assembly 209 and thus restore normal operation to the stacking arm 185. The depressed pin 196 is returned to its normally keyed first position upon engagement of the end projecting through gear 195 with a restoring plate 210.

The drive means for the various components of the apparatus such as the conveyor belts, rolls, drums, discs, transfer arm, stacking arm and the like have not been described in detail, but are schematically illustrated in FIGS. 5 through 8. It suffices to say that all of the drive means are suitably connected to main drive motor 220, FIG. 7, with the respective drive means and their timing being accomplished by suitable drive connections schematically illustrated in the various figures.

In the drawings and specification, there has been set forth a preferred embodiment of the invention and, although specific terms are employed, they are used in a generic and descriptive sense only and not for purposes of limitation.

What is claimed is:

[1. An apparatus for successively forming disposable diapers wherein the diaper includes a fluid permeable front cover sheet, a moisture absorbent pad superimposed on the front cover sheet and a backing sheet superimposed on the other side of the pad and secured to the front cover sheet along longitudinal and transverse edges thereof, said apparatus comprising means for supplying an elongate moisture absorbent pad comprising a batt of fibrous material and for feeding it along a substantially predetermined longitudinal path of travel, suction means for removing transverse segments of the batt of fibrous material at predetermined longitudinally spaced intervals, means cooperating with said pad supplying and feeding means for supplying and positioning an elongate fluid permeable front cover sheet in superimposed relation to one side of the pad, means cooperating with said pad supplying and feeding means for supplying and positioning a backing sheet in superimposed relation to the other side of the pad, means cooperating with said pad, front cover sheet and backing sheet supplying, positioning and feedmeans for receiving and feeding the superimposed front cover sheet, pad and backing sheet along a predetermined longitudinal path of travel, means cooperating with said receiving and feeding means for longitudinally sealing the side portions of the front cover sheet, pad and backing sheet in superimposed relation, means cooperating with said receiving and feeding means for transversely sealing the front cover sheet, pad and backing sheet in superimposed relation at predetermined longitudinally spaced intervals in registry with the removed transverse segments of the fibrous batt to form successively interconnected diapers, and means coperating with said transverse sealing means for severing the successively interconnected diapers along successive transverse seals to form individual diapers.]

[2. An apparatus, as set forth in claim 1, wherein said pad supplying and feeding means comprises means for supplying at least one elongate moisture absorbent sheet and feeding it along a substantially predetermined longitudinal path of travel, means for supplying an elongate web of moisture absorbent fibrous material and feeding it along a substantially predetermined path of travel, a fiberizing chamber disposed in the path of the fibrous web for receiving and fiberizing the web into generally individual fibers, and means including suction means communicating with said fiberizing chamber for withdrawing the fiberized fibers therefrom and depositing the fibers in superimposed batt form on a longitudinally extending central portion of the at least one moisture absorbent sheet to form the moisture absorbent pad.]

[3. An apparatus as set forth in claim 2, wherein said pad supplying and feeding means includes means for supplying an additional elongate moisture absorbent sheet and positioning it in superimposed relation to the other side of the fiber batt.]

4. An apparatus as set forth in claim [3] including severing means for trimming superimposed longitudinal side portions from the moisture absorbent sheets, and means for positioning the trimmed side portions in a superimposed, generally centrally located relation to the moisture absorbent sheets and fiber batt.

5. An apparatus, as set forth in claim *20* [1], including means cooperating with said front cover sheet supplying and positioning means for applying adhesive to the side of the front cover sheet that is positioned in superimposed relation to the pad to facilitate the securement of the front cover sheet to the pad.

6. An apparatus, as set forth in claim *20* [1], wherein the backing sheet has a width in excess of the width of the moisture absorbent pad and front cover sheet and wherein said apparatus further includes a folding means cooperating with said receiving and feeding means for folding opposite longitudinal side portions of the backing sheet around longitudinal side edges of the pad and front cover sheet for securing by said longitudinal sealing means.

7. An apparatus, as set forth in claim 6, wherein said longitudinal sealing means comprises means for applying adhesive to opposite marginal longitudinal side portions of the front cover sheet prior to folding of opposite longitudinal side portions of the backing sheet in overlapping relation to the marginal side portions of the front cover sheet, and means for compressing the overlapping side portions of the front cover sheet and backing sheet together to facilitate the securement thereof by the adhesive.

8. An apparatus, as set forth in claim *20* [1], wherein said transverse sealing means comprises embossing means disposed adjacent the predetermined path of travel of the superimposed front cover sheet, pad and backing sheet and being operative in timed relationship with said receiving and feeding means for transversely embossing the superimposed front cover sheet, pad and backing sheet at predetermined longitudinally spaced intervals.

9. An apparatus, as set forth in claim 8 wherein said severing means includes means cooperating with said embossing means for perforating the superimposed front cover sheet, pad and backing sheet transversely thereof along successive transverse seals.

10. An apparatus, as set forth in claim *20* [1], including means for folding opposite longitudinal side portions of the successively interconnected diapers inwardly over the central portion of same along first longitudinally extending fold lines and outer sections of the side portions outwardly back over inner sections of the side portions along second longitudinally extending fold lines to form a generally box pleat configuration.

11. An apparatus, as set forth in claim 10, wherein said last named folding means comprises means for folding opposite longitudinal side portions of the successively interconnected diapers along first longitudinally extending fold lines to extend substantially perpendicular to the central portion of same, and means for inwardly folding the opposite longitudinal side portions along second longitudinally extending fold lines positioned intermediate the first fold lines and side edges of same with the outer sections of the side portions overlapping inner sections of the side portions.

12. An apparatus, as set forth in claim 10, wherein said severing means comprises means cooperating with said transverse sealing means for perforating the superimposed front cover sheet, pad and backing sheet transversely thereof along successive transverse seals, and conveyor means positioned in receiving relation to said feeding means and folding means for receiving the successively interconnected diapers from said feeding means after folding thereof by said last named folding means and feeding same along a predetermined path of travel, said conveyor means advancing the same at a faster rate than said feeding means so as to separate the successively interconnected diapers along successive transverse perforations to form individual diapers.

13. An apparatus, as set forth in claim 12, wherein said conveyor means comprises a pair of superimposed cooperating continuous conveyors, said conveyors being disposed adjacent said feeding means for receiving the successively interconnected diapers therebetween, and including means cooperating with said feeding means and cooperating conveyors for transversely folding the same intermediate adjacent transverse seals and for transferring same to said cooperating conveyors.

14. An apparatus, as set forth in claim 13, including accumulating means disposed adjacent said cooperating conveyors for successively receiving the individual folded diapers therefrom and for positioning same in side-by-side relation.

15. An apparatus, as set forth in claim 14, wherein said accumulating means comprises an accumulating box having an accumulating portion and a receiving portion, said receiving portion being disposed adjacent said cooperating conveyors for successively receiving the individual folded diapers therefrom, and means for successively transferring the individual folded diapers from said receiving portion to said accumulating portion of said accumulating box and positioning same in said accumulating portion in side-by-side relation.

16. An apparatus, as set forth in claim 14, including means operatively associated with said accumulating means for selectively ejecting a folded diaper from said accumulating means.

17. An apparatus for successively forming disposable diapers wherein the diaper includes a fluid permeable front cover sheet, a moisture absorbent pad superimposed on the front cover sheet, and a backing sheet superimposed on the other side of the pad and secured to the front cover sheet along longitudinal and transverse edges thereof, said apparatus comprising means for supplying an elongate moisture absorbent pad and for feeding it along a substantially predetermined longitudinal path of travel, said means comprising means for supplying at least one elongate moisture absorbent sheet and feeding it along a substantially predetermined longitudinal path of travel, means for supplying an elongate web of moisture absorbent fibrous material and feeding it along a substantially predetermined path of travel, a fiberizing chamber disposed in the path of the fibrous web for receiving and fiberizing the web into generally individual fibers, means including suction means communicating with said fiberizing chamber for withdrawing the fiberized fibers therefrom and depositing the fibers in superimposed batt form on a longitudinally extending central portion of the at least one moisture absorbent sheet, additional suction means disposed adjacent the path of the at least one moisture absorbent sheet and superimposed fiber batt for removing transverse segments of the fiber batt at predetermined longitudinally spaced intervals, means for supplying an additional elongate moisture absorbent sheet and positioning it in superimposed relation to the other side of the fiber batt to form the moisture absorbent pad, means cooperating with said pad supplying and feeding means for supplying and positioning an elongate fluid permeable front cover sheet in superimposed relation to one side of the pad, means cooperating with said pad supplying and feeding means for supplying and positioning an elongate backing sheet in superimposed relation to the other side of the pad, means cooperating with said pad, front cover sheet and backing sheet supplying, positioning and feeding means for receiving and feeding the superimposed front cover sheet, pad and backing sheet along a predetermined longitudinal path of travel, means cooperating with said receiving and feeding means for longitudinally sealing the side portions of the front cover sheet, pad and backing sheet in superimposed relation, means cooperating with said receiving and feeding means and additional suction means for transversely sealing the front cover sheet, pad and backing sheet in superimposed relation at predetermined longitudinal spaced intervals in registry with the removed transverse segments of the fiber batt to form successively interconnected diapers, and means cooperating with said transverse sealing means for severing the successively interconnected diapers along successive transverse seals to form individual diapers.

18. An apparatus, as set forth in claim 17, wherein the backing sheet has a width in excess of the width of the pad and front cover sheet and wherein said apparatus further includes a folding means cooperating with said receiving and feeding means for folding opposite longitudinal side portions of the backing sheet around longitudinal edges of the pad and front cover sheet; and wherein said longitudinal sealing means comprises means for applying adhesive to opposite longitudinal side portions of the front cover sheet prior to folding of opposite side portions of the backing sheet in overlapping relation to the marginal side portions of the front cover sheet, and means for compressing the overlapping side portions of the front cover sheet and backing sheet together to facilitate the securement thereof by the adhesive; and wherein said transverse sealing means comprises embossing means disposed adjacent the predetermined path of travel of the superimposed front cover sheet, pad and backing sheet and being operative in timed relationship with said receiving and feeding means for transversely embossing the superimposed front cover sheet, pad and backing sheet at predetermined longitudinally spaced intervals.

19. An apparatus for successively forming disposable diapers wherein the diaper includes a fluid permeable front cover sheet, a moisture absorbent pad superimposed on the front cover sheet and a backing sheet superimposed on the other side of the pad and secured to the front cover sheet along longitudinal and transverse edges thereof, said apparatus comprising means for supplying an elongate moisture absorbent pad and for feeding it along a substantially predetermined longitudinal path of travel, means cooperating with said pad supplying and feeding means for supplying and positioning an elongate fluid permeable front cover sheet in superimposed relation to one side of the pad, means cooperating with said pad supplying and feeding means for supplying and positioning an elongate backing sheet in superimposed relation to the other side of the pad, means cooperating with said pad, front cover sheet and backing sheet supplying, positioning and feeding means for receiving and feeding the superimposed front cover sheet, pad and backing sheet along a predetermined longitudinal path of travel, means cooperating with said receiving and feeding means for longitudinally sealing the side portions of the front cover sheet, pad and backing sheet in superimposed relation, means cooperating with said receiving and feeding means for transversely sealing the front cover sheet, pad and backing sheet in superimposed relation at predetermined longitudinally spaced intervals to form successively interconnected diapers, means cooperating with said transverse sealing means for perforating the superimposed front cover sheet, pad and backing sheet transversely thereof along successive transverse seals, means cooperating with said receiving means and feeding means and transverse sealing means for folding opposite longitudinal side portions of the successively interconnected diapers inwardly over the central portion of same a long first longitudinally extending fold lines and outer sections of the side portions outwardly back over inner sections of side portions along second longitudinally extending fold lines, a pair of superimposed cooperating continuous conveyors disposed adjacent said feeding means and folding means for receiving the successively interconnected diapers therebetween and feeding same along a predetermined path of travel, said conveyor means advancing the same at a faster rate than said feeding means so as to separate the successively interconnected diapers along successive transverse seals, means cooperating with said receiving and feeding means and cooperating conveyors for transversely folding the successively interconnected diapers intermediate adjacent transverse seals and for transferring same to said cooperating conveyors, and accumulating means disposed adjacent said cooperating conveyors for successively receiving the individual folded diapers therefrom and for positioning same in side-by-side relation.

*20. An apparatus for successively forming disposable diapers wherein the diaper includes a fluid permeable front cover sheet, a moisture absorbent pad super-imposed on the front cover sheet and a backing sheet super-imposed on the other side of the pad and secured to the front cover sheet along longitudinal and transverse edges thereon, said apparatus comprising:*

*means for supplying an elongate moisture absorbent pad comprising a batt of fibrous materials and for feeding it along a substantially predetermined longitudinal path of travel, said pad supplying and feeding means comprising means for supplying at least one elongate moisture absorbent sheet and feeding it along a substantially predetermined longitudinal path of travel, means for supplying an elongate web of moisture absorbent fibrous material and feeding it along a substantially predetermined path of travel, a fiberizing chamber disposed in the path of the fibrous web for receiving and fiberizing the web into generally individual fibers, and means including suction means communicating with said fiberizing chamber for withdrawing the fiberized fibers therefrom and depositing the fibers in super-imposed batt form on a longitudinally extending central portion of the at least one moisture absorbent sheet to form the moisture absorbent pad;*

*means cooperating with said pad supplying and feeding means for supplying and positioning an elongate fluid permeable front cover sheet in super-imposed relation to one side of the pad;*

*means cooperating with said pad supplying and feeding means for supplying and positioning a backing sheet in super-imposed relation to the other said of the pad;*

*means cooperating with said pad, front cover sheet and backing sheet supplying, positioning and feeding means for receiving and feeding the super-imposed front cover sheet, pad and backing sheet along a predetermined longitudinal path of travel;*

*means cooperating with said receiving and feeding means for longitudinally sealing the side portions of the front cover sheet, pad and backing sheet in super-imposed relation;*

*means cooperating with said receiving and feeding means for transversely sealing the front cover sheet, pad and backing sheet in super-imposed relation at predetermined longitudinally spaced intervals to form successively interconnected diapers; and*

*means cooperating with said transverse sealing means for severing the successively interconnected diapers along successive transverse seals to form individual diapers.*

References Cited

The following references, cited by the Examiner, are of record in the patented file of this patent or the original patent.

UNITED STATES PATENTS

| | | | |
|---|---|---|---|
| 3,666,611 | 5/1972 | Joa | 156—213 X |
| 3,020,599 | 2/1962 | Pukis et al. | 19—144.5 |
| 2,283,137 | 5/1942 | Fine | 156—467 |
| 3,322,589 | 5/1967 | Joa | 156—461 |
| 2,916,037 | 12/1959 | Hansen | 128—284 |
| 3,474,592 | 10/1969 | Hessner | 128—284 X |
| 2,086,592 | 7/1937 | Williams | 156—377 X |
| 3,179,023 | 4/1965 | Hoff | 156—554 X |
| 3,430,629 | 3/1969 | Murphy | 128—284 |
| 2,131,808 | 10/1938 | Joa | 156—464 X |
| 3,510,587 | 5/1970 | Marder et al. | 128—284 |

FOREIGN PATENTS

| | | | |
|---|---|---|---|
| 884,195 | 12/1961 | Great Britain | 19—144.5 |

CHARLES E. VAN HORN, Primary Examiner

D. A. SIMMONS, Assistant Examiner

U.S. Cl. X.R.

19—144; 128—283; 156—552

UNITED STATES PATENT OFFICE

CERTIFICATE OF CORRECTION

Patent No. Re. 28,139 Dated August 27, 1974

Inventor(s) Graves T. Gore

It is certified that error appears in the above-identified patent and that said Letters Patent are hereby corrected as shown below:

Column 1, Line 59, "receiving" should be --received--;

Column 2, Line 19, "supplynig" should be --supplying--;

Column 4, Line 32, "transversea" should be --transverse--;

Column 4, Line 73, "aliging" should be --aligning--;

Column 6, Line 15, after "Thus," insert --upon--;

Column 6, Line 54, "circumstance" should be --circumference--;

Column 6, Line 72, "facilitates" should be --facilitate--;

Column 9, Line 9, after "cover" insert --sheet--

Column 12, Line 8, "coperating" should be --cooperating--;

Column 12, Line 34, after "claim" insert --20--;

Column 16, Line 26, "said" should be --side--.

Signed and sealed this 26th day of November 1974.

(SEAL)
Attest:

McCOY M. GIBSON JR.
Attesting Officer

C. MARSHALL DANN
Commissioner of Patents